(12) United States Patent
Popp et al.

(10) Patent No.: US 7,045,031 B2
(45) Date of Patent: May 16, 2006

(54) METHOD OF OPTIMIZING SPACING BETWEEN ELASTIC MEMBERS IN APPLYING LEG ELASTICS

(75) Inventors: Robert Lee Popp, Hortonville, WI (US); Joseph D. Coenen, Neenah, WI (US); Toan Thanh Le Minh, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 403 days.

(21) Appl. No.: 10/400,042

(22) Filed: Mar. 26, 2003

(65) Prior Publication Data

US 2003/0183325 A1    Oct. 2, 2003

Related U.S. Application Data

(62) Division of application No. 09/638,702, filed on Aug. 15, 2000, now Pat. No. 6,585,841.

(51) Int. Cl.
*B32B 37/00* (2006.01)

(52) U.S. Cl. .................. 156/176; 156/177; 156/178; 156/179

(58) Field of Classification Search ............. 156/160, 156/161, 163, 164, 166, 176, 177, 178, 179, 156/436, 439, 440, 441; 604/373, 385.24, 604/385.25, 385.26, 385.27
See application file for complete search history.

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,371,668 A | 3/1968 | Johnson | 128/290 |
| 3,468,748 A | 9/1969 | Bassett | 161/122 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,061,063 A | 12/1977 | Brush | 83/55 |
| 4,300,562 A | 11/1981 | Pieniak | 128/287 |
| 4,300,967 A | 11/1981 | Sigl | 156/164 |
| 4,340,563 A | 7/1982 | Appel et al. | 264/518 |
| 4,371,417 A | 2/1983 | Frick et al. | 156/495 |
| 4,397,704 A | 8/1983 | Frick | 156/201 |
| 4,412,881 A | 11/1983 | Sigl | 156/164 |
| 4,432,823 A | 2/1984 | Moore | 156/164 |
| 4,486,192 A | 12/1984 | Sigl | 604/385 |

(Continued)

FOREIGN PATENT DOCUMENTS

CA    1338133    3/1996 ................. 117/26

(Continued)

*Primary Examiner*—Gladys J P Corcoran
(74) *Attorney, Agent, or Firm*—Pauley Petersen & Erickson

(57) ABSTRACT

A method of applying leg elastics to absorbent garments involves optimizing the spacing between multiple elastic members. The elastic members are bonded to a substrate with variable spacing along the length of the leg opening. More particularly, narrower spacing is provided in the crotch area, thereby providing higher gasketing pressure, while wider spacing is provided in areas outside the crotch area for lower gasketing pressure and greater comfort. Alternatively, narrower spacing can be applied to the back portion of the leg, with medium spacing in the crotch area and wider spacing in the front portion or the leg, or conversely, wider spacing in the back portion with medium spacing in the crotch area and narrower spacing in the front portion, depending on the wearer's needs. The resulting garments have optimized comfort, fit and containment about the leg openings.

20 Claims, 8 Drawing Sheets

U.S. PATENT DOCUMENTS

| | | | |
|---|---|---|---|
| 4,578,133 A | 3/1986 | Oshefsky et al. | 156/164 |
| 4,610,681 A | 9/1986 | Strohbeen et al. | 604/396 |
| 4,617,082 A | 10/1986 | Oshefsky et al. | 156/447 |
| 4,639,949 A | 2/1987 | Ales et al. | 2/400 |
| 4,641,381 A | 2/1987 | Heran et al. | 2/400 |
| 4,642,819 A | 2/1987 | Ales et al. | 2/400 |
| 4,646,362 A | 3/1987 | Heran et al. | 2/400 |
| 4,648,928 A | 3/1987 | Ales | 156/164 |
| 4,650,532 A | 3/1987 | Kloehn et al. | 156/204 |
| 4,663,220 A | 5/1987 | Wisneski et al. | 428/221 |
| 4,675,016 A | 6/1987 | Meuli et al. | 604/385 A |
| 4,687,477 A | 8/1987 | Suzuki et al. | 604/385 A |
| 4,726,873 A | 2/1988 | Ales et al. | 156/495 |
| 4,743,241 A | 5/1988 | Igaue et al. | 604/385 A |
| 4,747,846 A | 5/1988 | Boland et al. | 604/38 A |
| 4,786,346 A | 11/1988 | Ales et al. | 156/160 |
| 4,863,542 A | 9/1989 | Oshefsky et al. | 156/160 |
| 4,915,767 A | 4/1990 | Rajala et al. | 156/440 |
| 4,917,746 A | 4/1990 | Kons et al. | 156/161 |
| 4,940,464 A | 7/1990 | Van Gompel et al. | 604/396 |
| 4,943,340 A | 7/1990 | Ujimoto et al. | 156/496 |
| 4,946,539 A | 8/1990 | Ales et al. | 156/495 |
| 5,046,272 A | 9/1991 | Vogt et al. | 38/143 |
| 5,055,103 A | 10/1991 | Nomura et al. | 604/385.2 |
| 5,092,861 A | 3/1992 | Nomura et al. | 604/385.2 |
| 5,104,116 A | 4/1992 | Pohjola | 271/185 |
| 5,143,679 A | 9/1992 | Weber et al. | 264/288.8 |
| 5,147,487 A | 9/1992 | Nomura et al. | 156/164 |
| 5,156,793 A | 10/1992 | Buell et al. | 264/288.8 |
| 5,167,897 A | 12/1992 | Weber et al. | 264/288.8 |
| 5,171,388 A | 12/1992 | Hoffman et al. | 156/164 |
| 5,180,534 A | 1/1993 | Thomas et al. | 264/145 |
| 5,213,645 A | 5/1993 | Nomura et al. | 156/164 |
| 5,224,405 A | 7/1993 | Pohjola | 83/24 |
| 5,226,992 A | 7/1993 | Morman | 156/62.4 |
| 5,230,851 A | 7/1993 | Thomas | 264/145 |
| 5,259,902 A | 11/1993 | Muckenfuhs | 156/164 |
| 5,275,676 A | 1/1994 | Rooyakkers et al. | 156/164 |
| 5,318,741 A | 6/1994 | Thomas | 264/519 |
| 5,326,415 A | 7/1994 | Thomas et al. | 156/244.11 |
| 5,334,152 A | 8/1994 | Nomura et al. | 604/385.2 |
| 5,342,341 A | 8/1994 | Igaue et al. | 604/385.2 |
| 5,354,400 A | 10/1994 | Lavash et al. | 156/227 |
| 5,385,706 A | 1/1995 | Thomas | 264/519 |
| 5,389,173 A | 2/1995 | Merkatoris et al. | 156/164 |
| 5,393,360 A | 2/1995 | Bridges et al. | 156/73.3 |
| 5,407,507 A | 4/1995 | Ball | 156/163 |
| 5,413,654 A | 5/1995 | Igaue et al. | 156/161 |
| 5,447,508 A * | 9/1995 | Numano et al. | 604/385.27 |
| 5,454,803 A | 10/1995 | Sageser et al. | 604/385.2 |
| 5,500,075 A | 3/1996 | Herrmann | 156/494 |
| 5,503,919 A | 4/1996 | Litchholt et al. | 428/286 |
| 5,509,985 A | 4/1996 | Kock | 156/160 |
| 5,516,392 A | 5/1996 | Bridges et al. | 156/160 |
| 5,517,737 A | 5/1996 | Viltro et al. | 26/88 |
| 5,518,566 A | 5/1996 | Bridges et al. | 156/161 |
| 5,525,175 A * | 6/1996 | Blenke et al. | 156/161 |
| 5,540,672 A | 7/1996 | Roessler et al. | 604/385.2 |
| 5,547,531 A | 8/1996 | Allen et al. | 156/164 |
| 5,622,578 A | 4/1997 | Thomas | 156/66 |
| 5,660,664 A | 8/1997 | Herrmann | |
| 5,662,636 A | 9/1997 | Benjamin et al. | 604/385.2 |
| 5,704,930 A | 1/1998 | Lavash et al. | 604/385.2 |
| 5,723,087 A | 3/1998 | Chappell et al. | 264/284 |
| 5,733,401 A | 3/1998 | Linman et al. | 156/160 |
| 5,745,922 A | 5/1998 | Rajala et al. | 2/243.1 |
| 5,749,865 A | 5/1998 | Yamamoto et al. | 604/385.2 |
| 5,749,989 A | 5/1998 | Linman et al. | 156/160 |
| 5,772,825 A | 6/1998 | Schmitz | 156/164 |
| 5,776,121 A | 7/1998 | Roe et al. | 604/385.1 |
| 6,569,275 B1 * | 5/2003 | Popp et al. | 156/229 |
| 6,585,841 B1 * | 7/2003 | Popp et al. | 156/161 |
| 6,635,041 B1 * | 10/2003 | Popp et al. | 604/385.25 |
| 6,689,115 B1 * | 2/2004 | Popp et al. | 604/385.27 |
| 6,808,582 B1 * | 10/2004 | Popp et al. | 156/229 |

FOREIGN PATENT DOCUMENTS

| | | |
|---|---|---|
| EP | 0 217 032 | 4/1987 |
| GB | 2 248 380 | 4/1992 |
| JP | 06 070958 | 3/1994 |
| JP | 10 211230 | 8/1998 |
| JP | 11 036103 | 2/1999 |
| JP | 11 332913 | 7/1999 |
| JP | 11 253487 | 9/1999 |
| JP | 2000 197663 | 7/2000 |
| JP | 2000 201970 | 7/2000 |
| WO | WO 9717921 A1 * | 5/1997 |

* cited by examiner

METHOD OF OPTIMIZING SPACING BETWEEN ELASTIC MEMBERS IN APPLYING LEG ELASTICS

This Application is a divisional of prior application Ser. No. 09/638,702, filed Aug. 15, 2000, now U.S. Pat. No. 6,585,841.

FIELD OF THE INVENTION

This invention is directed to a method of optimizing spacing between elastic members, thereby optimizing gasketing pressure distribution, in the application of leg elastics to a garment. The method involves adjusting pivot arm alignment and elastic guide location.

BACKGROUND OF THE INVENTION

Pant-like absorbent garments, such as diapers and training pants, typically include a pair of leg openings having an elastic portion around each leg opening. The elastic portions are intended to fit snugly around a wearer's legs to prevent leakage from the garment. However, more gasketing pressure is required in certain areas around the leg, such as in the crotch area, than in other areas around the leg, such as in the dwell areas away from the crotch.

Various technologies are known for applying leg elastics to such articles. For example, some technologies involve increasing spacing between elastic members at the crotch area around each leg opening. This type of spacing results in low gasketing pressure in the crotch area and higher gasketing pressure in the areas away from the crotch. This type of spacing is the normal process fallout due to the correspondence between the angle of application and the spacing between the elastic members.

More particularly, when the elastic members are applied to a garment in a machine direction, variations in the angle of application result in variations in spacing. When a device used to apply the elastic members aligns the elastic members in the crotch area in a row substantially perpendicular to the machine direction, as the elastic members are guided away from the crotch area, the angle between the row and the machine direction is closer to 0°, thereby resulting in wider spacing in the crotch area and narrower spacing in the area away from the crotch. Other technologies boast consistent spacing between elastic members around the entire leg opening. Some of the technologies mentioned, and others, include consistent gasketing pressure around the entire leg opening.

There is a need or desire for a process for optimizing spacing among elastic members around the leg openings of pant-like absorbent garments to provide enhanced comfort, fit and containment about the leg openings of such garments.

SUMMARY OF THE INVENTION

It has been found that variations in spacing among elastic members, other than the normal process fallout, are factors that can be optimized to provide enhanced comfort, fit and containment about the leg openings.

The present invention is directed to a method of applying leg elastics to pant-like absorbent garments using variable spacing among the elastic members. More specifically, gasketing pressure distribution around a wearer's legs is optimized by changing the spacing between the elastic members, and curving the leg elastics at the same time to optimize the performance of the leg elastics for enhanced comfort, fit and containment.

In one embodiment of the invention, a pivot arm parallel to a substrate as the substrate is fed through a pair of nip rolls is used to carry out the method of the invention. Furthermore, the pivot arm includes elastic guides spaced at different radii from a pivot point on the pivot arm. This invention can provide customized higher gasketing pressure anywhere in the leg area for higher gasketing, and lower gasketing pressure over any area in the leg area for better comfort. These areas can be customized in any shape on the product which would offer an ideal fit all the way around the leg. For example, a resulting absorbent garment can have narrow spacing over a back part of the leg, medium spacing in the crotch area, and wide spacing over a front part of the leg away from the crotch area.

In another embodiment of the invention, a pivot arm which is perpendicular to a substrate as the substrate is fed through a pair of nip rolls is used to carry out the method of the invention. In this embodiment, the pivot arm also includes elastic guides spaced at different radii from a pivot point on the pivot arm. A resulting absorbent garment can have narrow spacing in the crotch area and wide spacing in the area away from the crotch.

In yet another embodiment of the invention, a linear arm which is perpendicular to a substrate as the substrate is fed through a pair of nip rolls, with elastic guides on a rotating pivot guide on the arm, is used to carry out the method of the invention. In this case, a resulting absorbent garment can also have narrow spacing in the crotch area and wide spacing in the area away from the crotch.

With the foregoing in mind, it is a feature and advantage of the invention to provide a method of applying leg elastics to an absorbent garment resulting in optimized performance of the leg elastics in terms of comfort, fit and containment.

It is another feature and advantage of the invention to provide a method of tailoring leg elastic spacing in an absorbent garment to optimize gasketing pressure to fit a wearer's body.

DEFINITIONS

Figure 1:
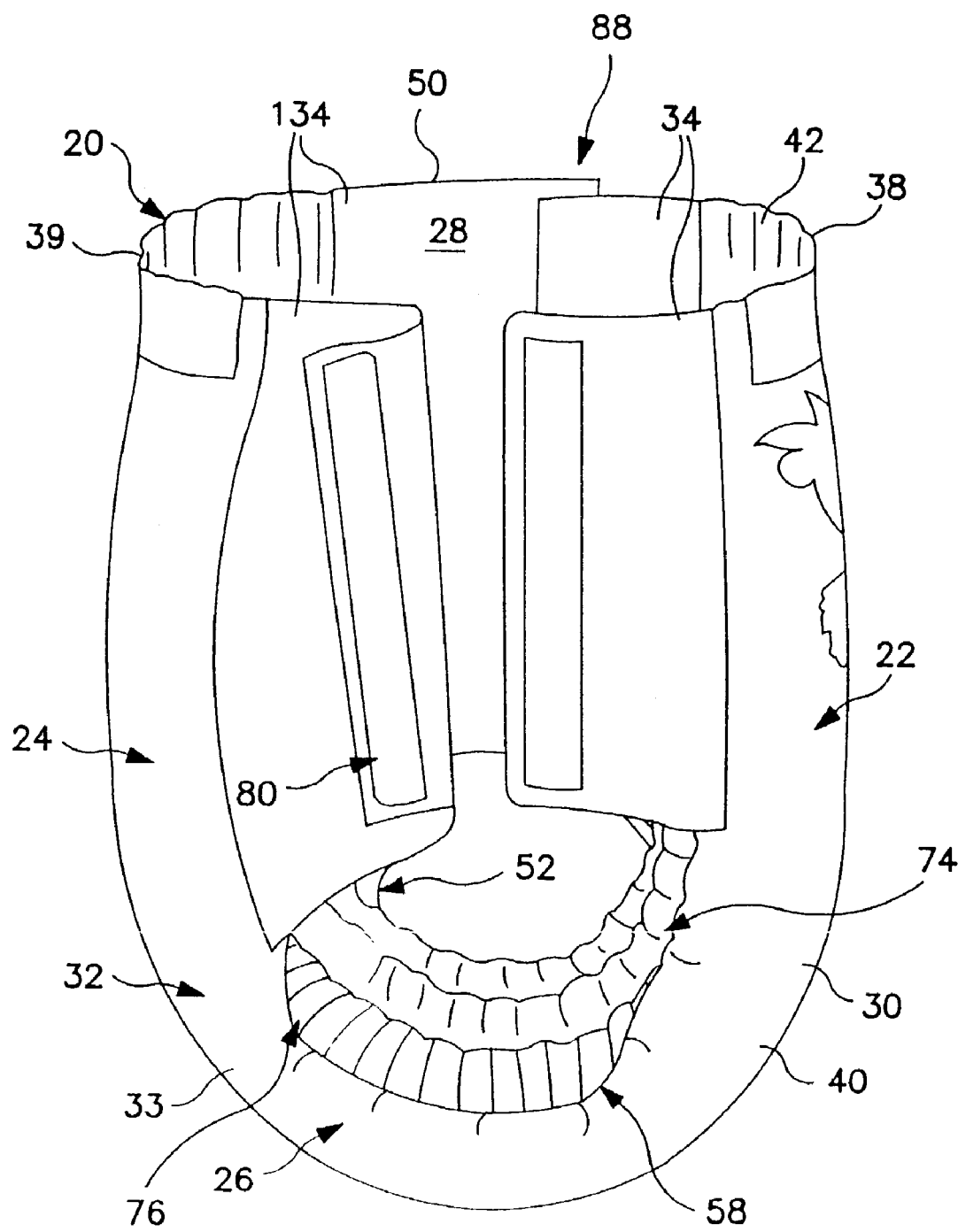
FIG. 1 is a side perspective view of an absorbent garment.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. The term includes apertured films, slit films, and other porous films which constitute liquid 110 transfer films, as well as films which do not transfer liquid. The term also includes film-like materials that exist as open-celled foams.

"Force" includes a physical influence exerted by one body on another which produces acceleration of bodies that are free to move and deformation or separation of bodies that are not free to move.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Layer" when used in the singular can have the dual meaning of a single element or a plurality of elements.

"Leg elastic" includes elastic bands, strands, ribbons, filaments, filament bunches and the like, which are adjacent to a garment opening that receives a wearer's leg.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid-permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 2:
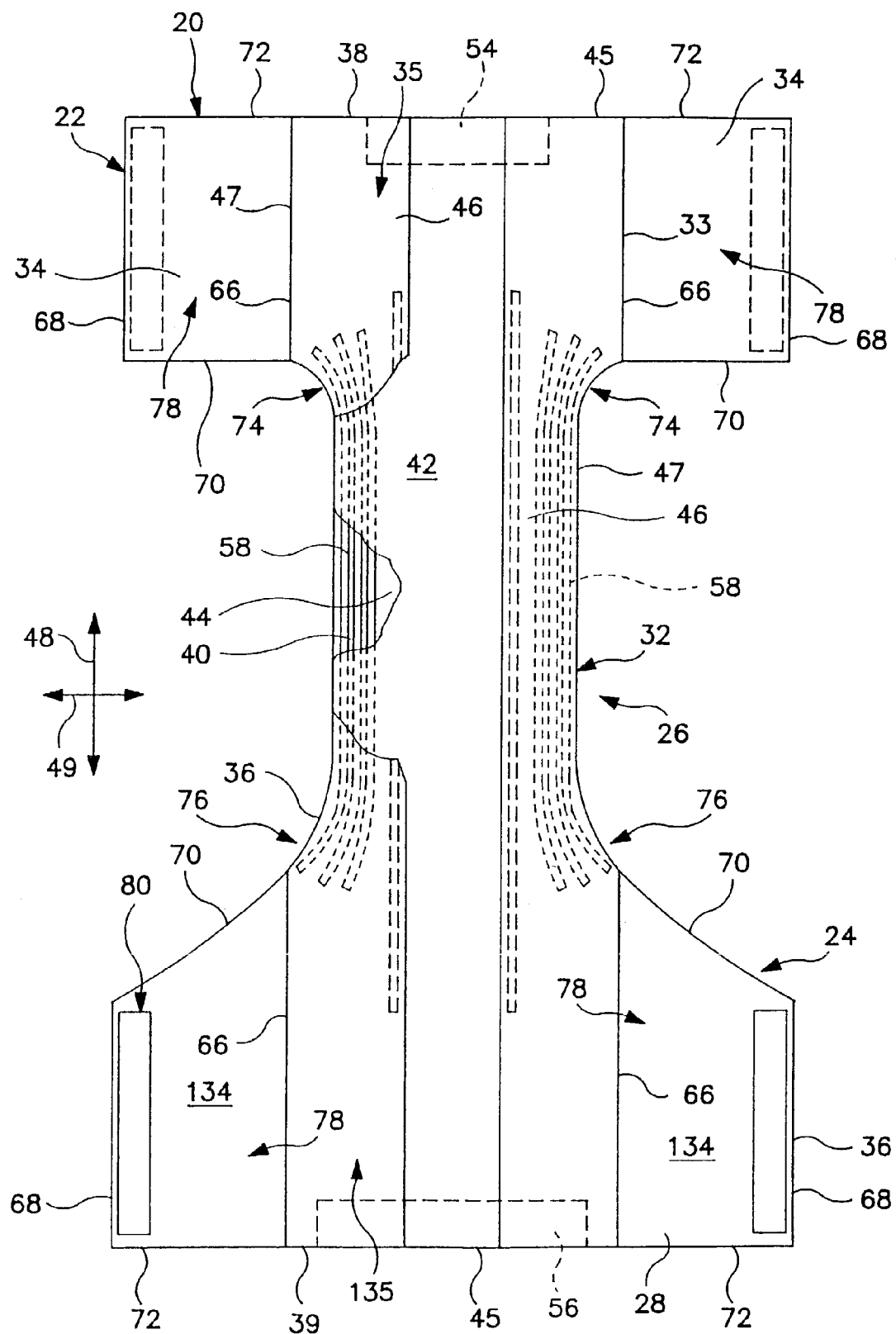
FIG. 2 is a plan view of the absorbent garment of FIG. 1 in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes depicted in FIG. 2. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the composite. The joining, attaching, connecting or the like can be either directly, such as joining either member directly to an element, or can be indirectly by means of another member disposed between the first member and the first element, or can be such that the first member is mechanically trapped by adjacent bond points in the first element such that the first member causes the composite to exhibit characteristics of the first member.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Pressure" is defined as force per unit area as applied to the wearer's skin to provide gasketing.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The principles of the present invention can be incorporated into any suitable disposable absorbent article. Examples of such suitable articles include diapers, training pants, feminine hygiene products, incontinence products, other personal care or health care garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Referring to FIG. 1, a disposable absorbent article, such as a training pant 20, is illustrated in a partially fastened condition. The training pant 20 includes an absorbent chassis 32 and leg elastic members 58. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIG. 2, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

The illustrated absorbent chassis 32 includes a somewhat rectangular composite structure 33, a pair of transversely opposed front side panels 34, and a pair of transversely opposed back side panels 134. The composite structure 33 and side panels 34 and 134 may be integrally formed or may include two or more separate elements, as shown in FIG. 2. The illustrated composite structure 33 includes an outer cover 40, a bodyside liner 42 which is connected to the outer cover in a superposed relation, an absorbent assembly 44 which is located between the outer cover 40 and the bodyside liner 42, and a pair of containment flaps 46. The rectangular composite structure 33 has opposite linear end edges 45 that form portions of the front and back waist edges 38 and 39, and opposite linear side edges 47 that form portions of the side edges 36 of the absorbent chassis 32. Leg openings 52 (FIG. 1) are generally defined by portions of the transversely opposed side edges 36 in the crotch region 26. For reference, arrows 48 and 49 depicting the orientation of the longitudinal axis and the transverse axis, respectively, of the training pant 20 are illustrated in FIG. 2.

Figure 3:
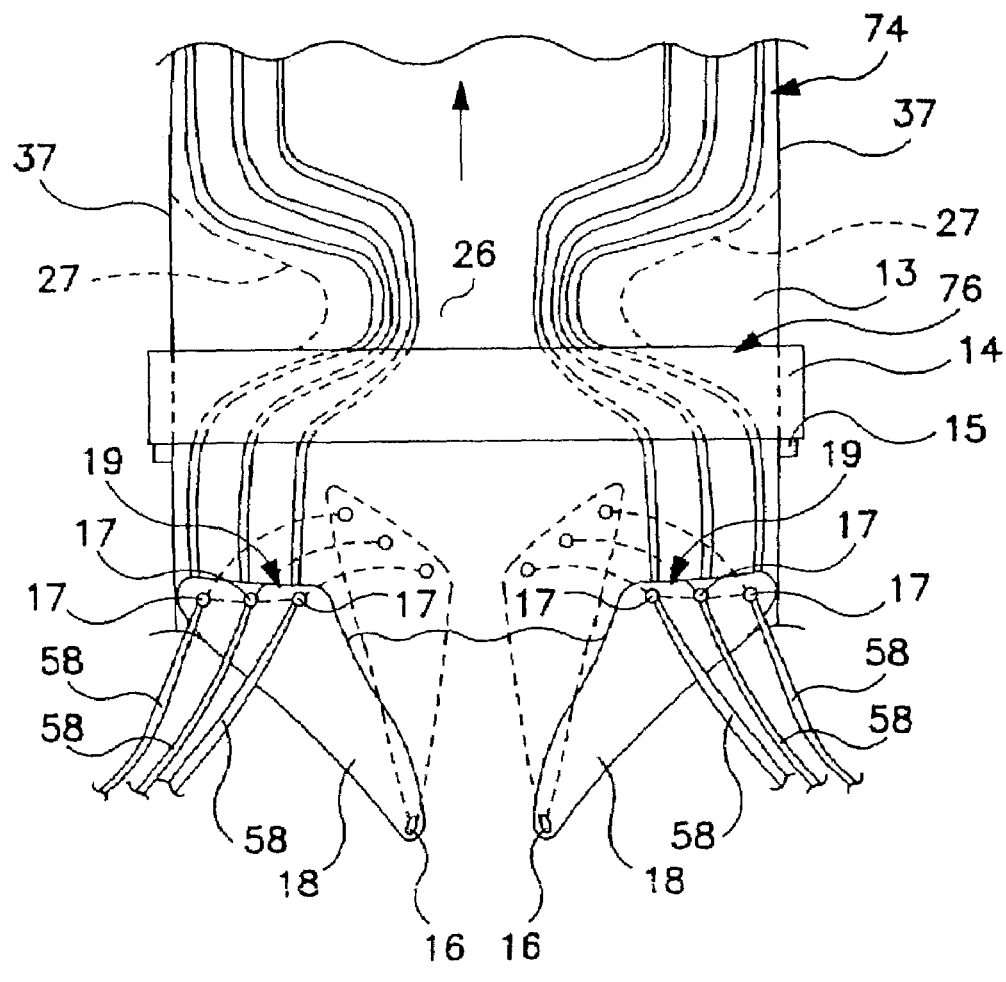
FIG. 3 is a top plan view of apparatus used for applying leg elastics to an absorbent garment according to one embodiment of the invention.
Figure 5:
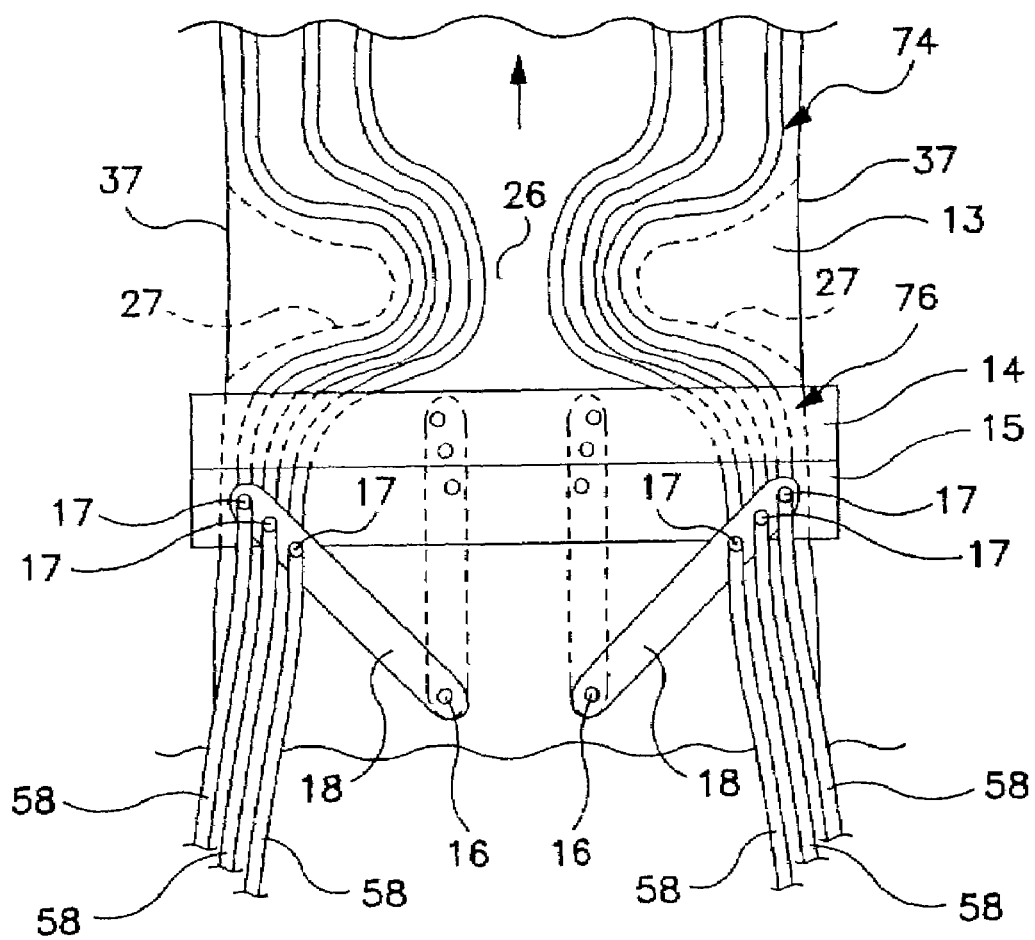
FIG. 5 is a top plan view of apparatus used for applying leg elastics to an absorbent garment according to a second embodiment of the invention.

The leg elastic members 58 are operatively joined to the outer cover 40 and/or bodyside liner 42 along the opposite edges 36 and positioned in the crotch region 26 of the training pant 20 to prevent leakage. When spacing between the leg elastic members 58 is optimized, as in the present invention, the performance of the leg elastic members 58, in terms of comfort, fit and containment, is also optimized. One example of optimized spacing includes narrow spacing between the leg elastic members 58 in the crotch region 26 and wider spacing in areas outside the crotch region 26, as shown in FIG. 3. Such spacing provides higher gasketing in the crotch region 26 and lower gasketing pressure over a front area 74 and a back area 76 of the leg openings 52 (FIG. 1) for better comfort. Another example of optimized spacing includes narrow spacing over a back area 76 of the leg openings 52, medium spacing in the crotch region 26, and wide spacing over the front area 74 of the leg openings 52 away from the crotch region 26, as shown in FIG. 5. This manner of spacing provides higher gasketing in the back area 76 of the leg openings 52 and added comfort in the front area 74 of the leg openings 52.

Narrow spacing between adjacent elastic members is preferably, but not necessarily, in the range of 0 to 0.25 cm. Medium spacing between adjacent elastic members is preferably between 0.26 and 0.50 cm. Wide spacing between adjacent elastic members is preferably, but not necessarily, in the range of 0.51 to 1.5 cm. Because the terms "narrower" and "wider" spacing are relative, and determined with respect to each other, they are not limited to precise dimension ranges. Generally, a region of wider spacing should have at least 10% more distance between the elastic members than a region of narrower spacing. Preferably, the difference in spacing should be at least 20%, more preferably at least 50%.

As used herein, the terms "crotch region" and "crotch area" refer to the area of the garment 20 located between a wearer's legs. The term "front area" refers to areas of the garment 20 located in front of a wearer's legs. Similarly, the term "back area" refers to areas of the garment 20 located in back of a wearer's legs. The term "side area" refers to areas of the garment 20 located between the front area and the back area, opposite the crotch area. The term "outer area" includes any one or more of the "front area", "back area" or "side area".

Figure 4:
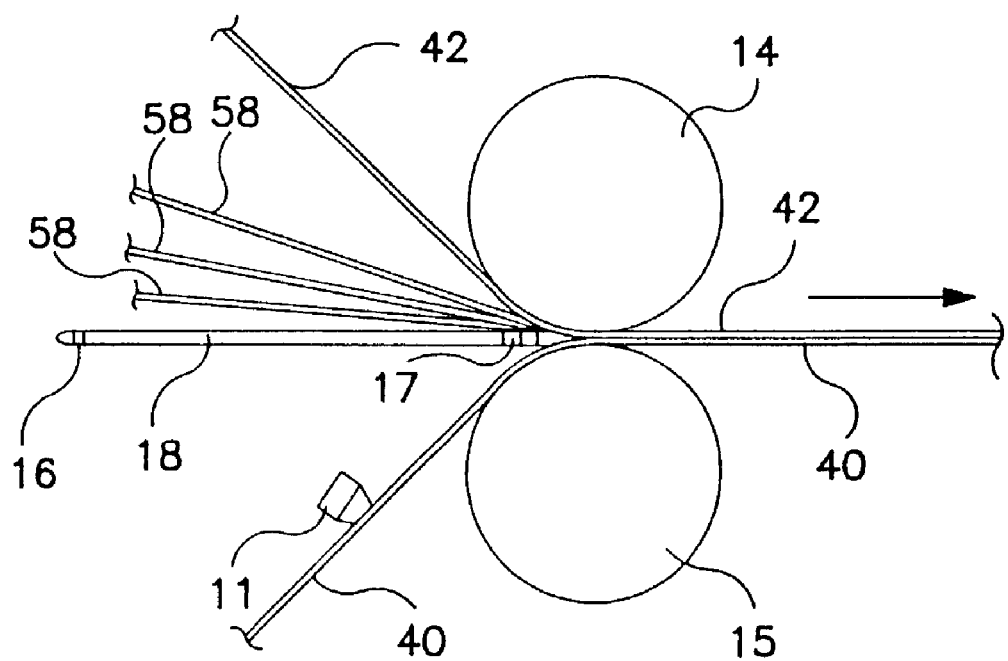
FIG. 4 is a side view of the apparatus of FIG. 3.

One example of apparatus for carrying out the invention is shown generally in FIGS. 3 and 4. The apparatus 3 includes a pair of pivot arms 18 having elastic guide openings 17. The pivot arms 18 are preferably in a plane substantially parallel to a substrate 13 as the substrate is being fed through a pair of nip rolls 14 and 15 in a machine direction (indicated by the arrows in FIGS. 3–8), best illustrated in FIG. 4. The elastic guide openings 17 are spaced at different radii from a pivot point 16 on each of the pivot arms 18. The elastic guide openings 17 are preferably, but not necessarily, substantially evenly spaced apart from one another in a row 19 on each pivot arm 18. The leg elastic members 58 are fed through the elastic guide openings 17 and then bonded to the substrate 13 as the pivot arms 18 direct the elastic members 58 toward outer edges 37, or toward the crotch region 26, of the substrate 13 and the elastic members 58 are fed through the pair of nip rolls 14 and 15 in the machine direction (indicated by the arrows). Alternatively, the pivot arms 18 can pivot in a plane at an angle between parallel and perpendicular to the substrate 13. As used herein, the term "machine direction" refers to the primary direction of movement of continuously moving layers in the manufacturing process. Likewise, the term "cross machine direction" refers to the direction substantially normal to the machine direction.

Each elastic guide opening 17 on the pivot arm 18 preferably guides an individual leg elastic member 58. As the pivot arm 18 pivots, the resulting elastic member spacing is wider as the arm 18 moves in one direction and narrower as the arm 18 moves in the opposite direction. Spacing variations are caused by movement of the elastic guide openings 17. For example, when the elastic guide openings 17 on one pivot arm 18 are aligned in a row 19 substantially perpendicular to the machine direction, the spacing between the elastic members 58 is at its maximum width. Likewise, the closer the row 19 is to being parallel to the machine direction, the narrower the spacing will be. As the substrate 13 travels in the machine direction prior to passing through the pair of nip rolls 14 and 15, the leg elastic members 58 are bonded, also in the machine direction, along, near, or between outer edges 37 of the substrate 13. Leg contours 27 can be pre-cut along the outer edges 37 of the substrate 13 or may be cut along the contour of the leg elastic members 58 subsequent to the bonding process. The regions in which the leg elastic members 58 are bonded to the substrate 13 ultimately end up forming the leg openings 52 (FIG. 1).

The combination of the pivot point 16, the location of the elastic guide openings 17 with respect to the machine direction, and the location of the elastic guide openings 17 with respect to the cross machine direction for each elastic member 16 can provide a unique shape for the leg elastic members 58, preferably a unique shape that provides an ideal fit all the way around a wearer's leg. For example, a resulting absorbent garment 20 can have narrow spacing over the back area 76 of the leg openings 52, medium spacing in the crotch region 26, and wide spacing over the front area 74 of the leg openings 52 away from the crotch region 26, thereby providing higher gasketing (better leakage protection) in the areas having narrower spacing, and lower gasketing pressure for greater comfort in the areas having wider spacing. Likewise, another example of a product of this invention is an absorbent garment 20 having narrow spacing over the front area 74 of the leg openings 52, medium spacing in the crotch region 26, and wide spacing over the back area 76 of the leg openings 52 for higher gasketing (greater leakage protection) in the front of the garment 20. Transition spacing between areas away from the crotch region 26 is customized between the front and the back of the product to provide comfort, fit and containment. These areas can be customized in any shape on the product which would offer an ideal fit all the way around the leg.

Figure 6:
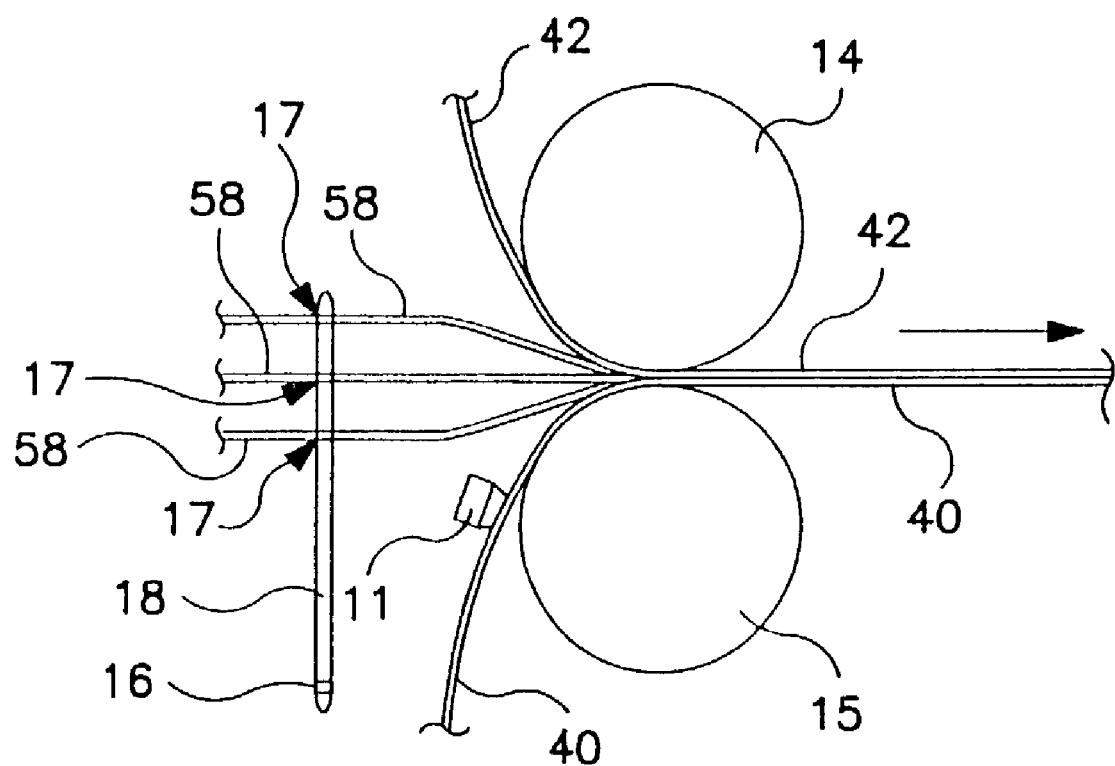
FIG. 6 is a side view of the apparatus of FIG. 5.

Another example of apparatus for carrying out the invention is shown generally in FIGS. 5 and 6. Like the apparatus 3 in FIGS. 3 and 4, this apparatus 3 includes a pair of pivot arms 18 having elastic guide openings 17 spaced at different radii from a pivot point 16 on each of the pivot arms 18. Instead of the pivot arms 18 pivoting in a plane substantially parallel to the substrate 13 as the substrate is being fed through the pair of nip rolls 14 and 15, this apparatus has the pivot arms 18 positioned to pivot in a plane substantially perpendicular to the substrate 13 as the substrate is being fed through the pair of nip rolls 14 and 15. A resulting absorbent garment 20 has narrow spacing in the crotch region 26 and wide spacing in the area away from the crotch region 26 with transition spacing somewhere between narrow and wide.

Figure 7:
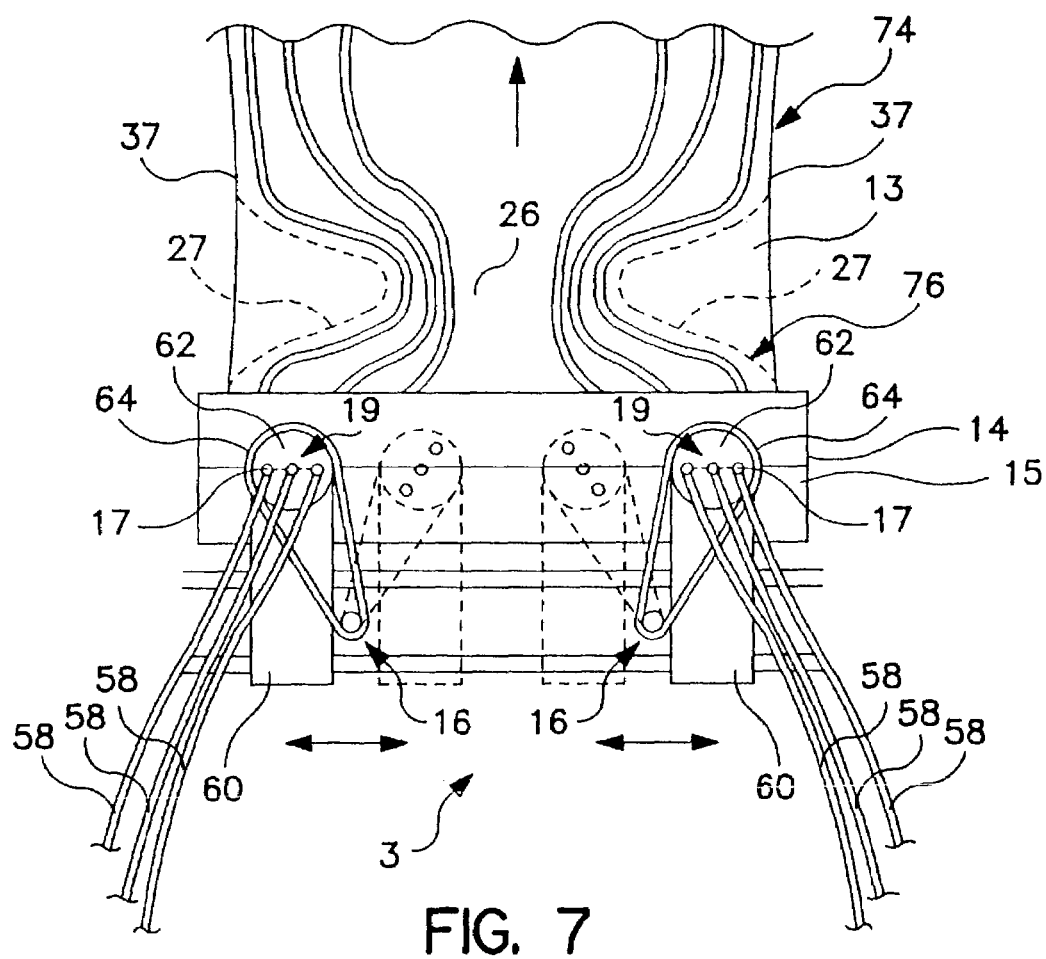
FIG. 7 is a top plan view of apparatus used for applying leg elastics to an absorbent garment according to a third embodiment of the invention.
Figure 8:
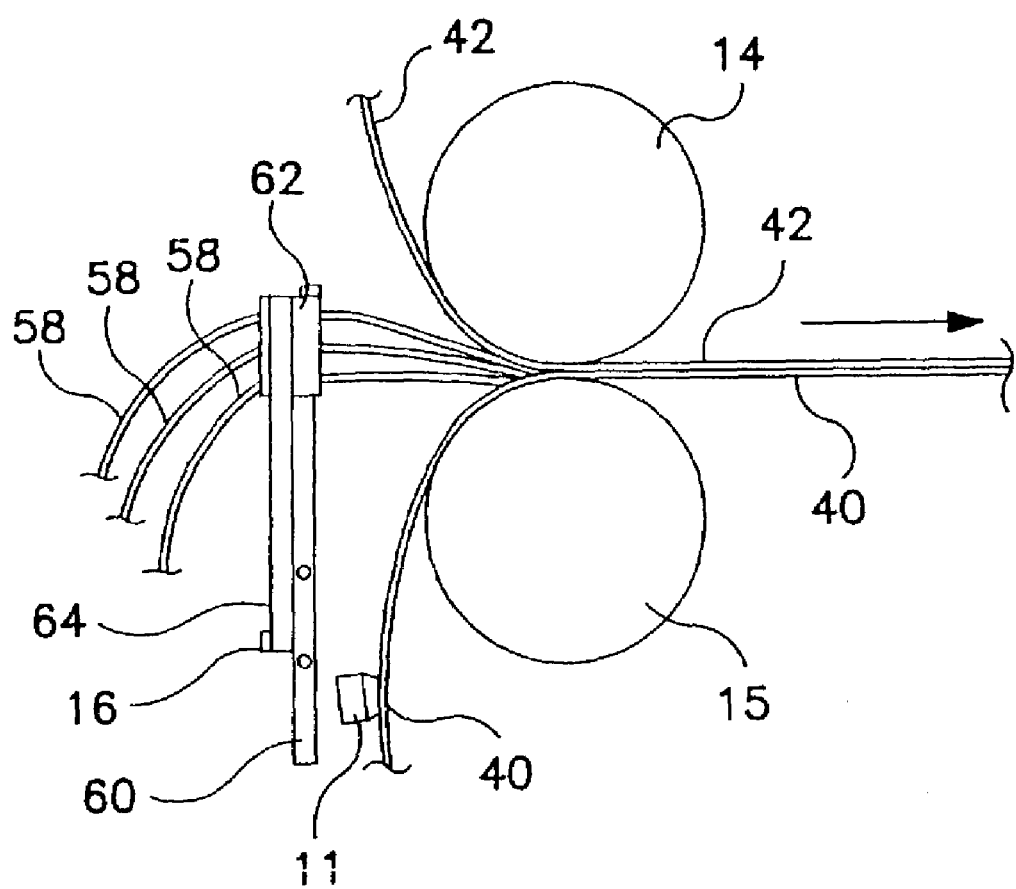
FIG. 8 is a side view of the apparatus of FIG. 7.

Yet another example of apparatus for carrying out the invention is shown generally in FIGS. 7 and 8. This apparatus 3 includes a pair of linear arms 60 each having a rotating pivot guide 62. The linear arms 60 are positioned such that they laterally slide in a plane substantially perpendicular to a substrate 13 as the substrate is being fed through a pair of nip rolls 14 and 15. The linear arms 60 move in a lateral, linear motion in a cross machine direction perpendicular to the machine direction of the substrate 13. The machine direction is indicated by the single-headed arrow and the cross machine direction is indicated by the double-headed arrows in FIG. 7. The rotating pivot guides 62 have individual elastic guide openings 17 for spacing the leg elastic members 58 apart from one another. A belt 64 is wrapped around the rotating pivot guide 62 at one end and around a stationary pivot point 16 at an opposite end. As the linear arm 60 moves back and forth, the belt 64 remains in place around the stationary pivot point 16 but causes the rotating pivot guide 62 to rotate in a pulley-like manner such that alignment of the row 19 of elastic guide openings 17 shifts. Alternatively, instead of the belt 64, other suitable rotating devices may be used, such as a cam system or a spring mounted rotating pivot guide with a connecting rod.

When the elastic guide openings 17 are aligned in a horizontal row 19 perpendicular to the machine direction, the leg elastic members 58 are spaced apart at a maximum distance. When the pivot guides 62 are pivoted and rotated clockwise or counter-clockwise, as indicated by the dotted lines, the angle of the row 19 of elastic guide openings 17 with respect to the machine direction determines the spacing between the leg elastic members 58 as the members 58 are bonded to the substrate 13. More particularly, when the elastic guide openings 17 are pivoted and rotated toward the crotch region 26, the guide openings 17 are aligned in a row 19 between 0° and 90° with respect to the machine direction. When the row 19 and the machine direction are at an angle closer to 90°, the leg elastic members 58 are spaced relatively wide apart. Likewise, when the row 19 and the machine direction are closer to being parallel, namely at an angle closer to 0°, the spacing between the leg elastic members 58 is relatively narrow.

The combination of both the linear motion in the cross machine direction along with the cross machine direction pivoting of the guide 62 on the linear arm 60 provides a unique shape for the leg elastic members 58 as the members 58 are bonded to the substrate 13. A resulting absorbent garment 20 has narrow spacing in the crotch region 26 and wide spacing in the areas furthest away from the crotch region 26, with transition spacing between narrow and wide spacing, thereby providing a customized fit around a wearer's leg with higher gasketing pressure for containment in the crotch region 26 and more comfort with less gasketing pressure in the other areas around the leg.

A wide variety of elastic materials may be used for the leg elastic members 58. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. A bonding device 11 is shown generally in FIGS. 4, 6 and 8. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The leg elastic members 58 preferably have a width of about 0.05 inch to about 3 inches, more preferably about 0.15 inch to about 1.5 inches, most preferably about 0.25 inch to about 1.0 inch. The leg elastic members 58 preferably have maximum elongation of 25–350%, more preferably about 30–260%, most preferably about 35–200%.

The substrate 13 is preferably the outer cover 40 and desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

As mentioned, the leg elastic members 58 can be bonded to the outer cover 40 and/or the bodyside liner 42. FIGS. 4, 6 and 8 show the leg elastic members 58 being bonded to the outer cover 40 and the bodyside liner 42 at the same time. In this embodiment, the leg elastic members 58 are essentially sandwiched between the outer cover 40 and the bodyside liner 42.

The liquid permeable bodyside liner 42 is illustrated as overlying the outer cover 40 and absorbent assembly 44 (FIG. 2), and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 2) is positioned between the outer cover 40 and the bodyside liner 42, which components can be joined together by any suitable means, such as adhesives, as is well known in the art. The absorbent assembly 44 can be any structure which is generally compressible, conformable, nonirritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 grams per square meter, and including a through-air-bonded-carded web of a homogenous blend of 60 percent 3 denier bicomponent fiber including a polyester core/polyethylene sheath, commercially available from BASF Corporation, and 40 percent 6 denier polyester fiber, commercially available from Hoechst Celanese Corporation, in Portsmouth, Va., U.S.A.

As noted previously, the illustrated training pant 20 has front and back side panels 34 and 134 disposed on each side of the absorbent chassis 32 (FIGS. 1 and 2). These transversely opposed front side panels 34 and transversely opposed back side panels 134 can be permanently bonded to the composite structure 33 of the absorbent chassis 32 in the respective front and back waist regions 22 and 24, and are releasably attached to one another by a fastening system 80. More particularly, as shown best in FIG. 2, the front side panels 34 can be permanently bonded to and extend transversely beyond the linear side edges 47 of the composite structure 33 in the front waist region 22 along attachment lines 66, and the back side panels 134 can be permanently bonded to and extend transversely beyond the linear side edges of the composite structure in the back waist region 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover or the bodyside liner.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material (See FIG. 2). Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis 49 of the training pant 20. In particular embodiments, the front and back side panels 34 and 134 may each include an interior portion 78 disposed between a distal edge 68 and a respective front or back center panel 35 or 135. In the illustrated embodiment in FIG. 2, the interior portions 78 are disposed between the distal edges 68 and the side edges 47 of the rectangular composite structure 33. The elastic material of the side panels 34 can be disposed in the interior portions 78 to render the side panels elastomeric in a direction generally parallel to the transverse axis 49. Most desirably, each side panel 34 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68 and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

The absorbent chassis 32 and the fastening system 80 together define a refastenable pant having a waist opening 50 and a pair of leg openings 52 (FIG. 1). When the fastening system is engaged, it can be appreciated that the refastenable pant includes a pair of elastomeric front side panels 34 extending from the waist opening to each leg opening, a pair of elastomeric back side panels 134 extending from the waist opening to each leg opening, a pair of refastenable seams 88 (FIG. 1) extending from the waist opening to each leg opening and positioned between the elastomeric front and back side panels, an elastomeric front waistband 54 (FIG. 2) disposed in the front waist region and positioned between the pair of elastomeric front side panels, an elastomeric back waistband 56 (FIG. 2) disposed in the back waist region and positioned between the pair of elastomeric back side panels, and at least a pair of elastomeric leg members 58 which partially encircle each leg opening. More preferably, more than one elastomeric leg member 58 partially or fully encircles each leg opening 52. Each elastomeric leg member 58 extends from adjacent an elastomeric front side panel 34 in the front waist region 22 to adjacent an elastomeric back side panel 134 in the back waist region 24.

As described herein, the various components of the training pant 20 can be integrally assembled together employing various types of suitable attachment means, such as adhesive, sonic and thermal bonds or combinations thereof. The resulting product is an absorbent garment having optimized comfort, fit and containment about the leg openings 52.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

The invention claimed is:

1. A method of attaching leg elastics to an absorbent garment, comprising the steps of:
    using a linear arm to guide a plurality of elastic members onto a substrate;
    sliding the linear arm toward a crotch area of the substrate;
    pivoting a rotating pivot guide on the linear arm to decrease spacing between the elastic members as the elastic members are projected on the crotch area of the substrate;
    sliding the linear arm toward an area of the substrate away from the crotch;
    pivoting the rotating pivot guide on the linear arm to increase spacing between the elastic members as the elastic members are projected on the area of the substrate away from the crotch; and
    bonding the elastic members to the substrate such that spacing between the elastic members is narrower in the crotch area than the spacing between the elastic members in at least one portion away from the crotch area.

2. The method of claim 1 wherein the linear arm guides at least three elastic members onto the substrate.

3. The method of claim 1 further comprising the step of simultaneously bonding the elastic members to a second layer of material while bonding the elastic members to the substrate.

4. The method of claim 1, further comprising the step of capturing the elastic members between the substrate and a second layer while bonding the substrate to the second layer.

5. The method of claim 1 further comprising the step of passing the elastic members and the substrate through a pair of nip rolls.

6. The method of claim 5 wherein the linear arm slides laterally in a plane substantially perpendicular to the substrate as the substrate is fed through the nip rolls.

7. The method of claim 1 wherein the linear arm is slid alternately toward the crotch area and toward the area away from the crotch area in a linear motion in a cross machine direction relative to a direction in which the substrate is traveling.

8. The method of claim 1 wherein the rotating pivot guide comprises an individual elastic guide for each elastic member and spaces the elastic members substantially in a row.

9. The method of claim 8 wherein the row of elastic members is substantially perpendicular with respect to a machine direction in which the substrate is traveling when the linear arm is aligned with the area away from the crotch area.

10. The method of claim 8 wherein the row of elastic members is at an angle between 0° and 90° with respect to a machine direction in which the substrate is traveling when the linear arm is aligned with the crotch area.

11. A method of attaching leg elastics to a garment, comprising the steps of:
    using a linear arm to guide a plurality of elastic members onto a substrate;
    sliding the linear arm toward a crotch area of the substrate;
    pivoting a rotating pivot guide on the linear arm to decrease spacing between the elastic members as the elastic members are projected on the crotch area of the substrate;
    sliding the linear arm toward an area of the substrate away from the crotch;
    pivoting the rotating pivot guide on the linear arm to increase spacing between the elastic members as the elastic members are projected on the area of the substrate away from the crotch; and
    bonding the elastic members to the substrate such that spacing between the elastic members is narrower in the crotch area than the spacing between the elastic members in at least one portion away from the crotch area.

12. The method of claim 11 wherein the linear arm guides at least three elastic members onto the substrate.

13. The method of claim 11 further comprising the step of simultaneously bonding the elastic members to a second layer of material while bonding the elastic members to the substrate.

14. The method of claim 11, further comprising the step of capturing the elastic members between the substrate and a second layer while bonding the substrate to the second layer.

15. The method of claim 11 further comprising the step of passing the elastic members and the substrate through a pair of nip rolls.

16. The method of claim 15 wherein the linear arm slides laterally in a plane substantially perpendicular to the substrate as the substrate is fed through the nip rolls.

17. The method of claim 11 wherein the linear arm is slid alternately toward the crotch area and toward the area away from the crotch area in a linear motion in a cross machine direction relative to a direction in which the substrate is traveling.

18. The method of claim 11 wherein the rotating pivot guide comprises an individual elastic guide for each elastic member and spaces the elastic members substantially in a row.

19. The method of claim 18 wherein the row of elastic members is substantially perpendicular with respect to a machine direction in which the substrate is traveling when the linear arm is aligned with the area away from the crotch area.

20. The method of claim 18 wherein the row of elastic members is at an angle between 0° and 90° with respect to a machine direction in which the substrate is traveling when the linear arm is aligned with the crotch area.

* * * * *